United States Patent [19]
Taylor

[11] 4,265,243
[45] May 5, 1981

[54] COLLECTION CONTAINER WITH SIPHON ASSEMBLY

[75] Inventor: Glenn N. Taylor, Cary, Ill.

[73] Assignee: The Kendall Company, Boston, Mass.

[21] Appl. No.: 26,868

[22] Filed: Apr. 4, 1979

[51] Int. Cl.³ ............................................. A61F 5/44
[52] U.S. Cl. .................................. 128/275; 128/760; 128/765; 128/767
[58] Field of Search ............... 128/272, 275, 276, 295, 128/DIG. 24, 760, 761, 762, 763, 765, 766, 767, 768, 228, 232, 227; 137/142, 147, 150; 141/114, 230; 222/204, 416; 4/110

[56] References Cited

U.S. PATENT DOCUMENTS

| | | | |
|---|---|---|---|
| 1,071,062 | 8/1913 | Lambden | 128/228 |
| 3,204,632 | 9/1965 | Hofstra et al. | 128/272 |
| 3,452,757 | 7/1969 | Ames | 128/232 |
| 3,683,894 | 8/1972 | Villari | 128/275 |
| 3,800,795 | 4/1974 | Walker | 128/275 |
| 3,888,126 | 6/1975 | Cross | 73/426 |
| 3,912,455 | 10/1975 | Lichtenstein | 128/762 |
| 3,943,929 | 3/1976 | Patel | 128/275 |
| 4,002,075 | 1/1977 | Cross | 73/426 |
| 4,015,605 | 4/1977 | McWhorter | 128/767 |
| 4,084,593 | 4/1978 | Jarund | 128/295 |
| 4,136,678 | 1/1979 | Beach | 128/232 |

Primary Examiner—Robert W. Michell
Assistant Examiner—J. L. Kruter
Attorney, Agent, or Firm—Powell L. Sprunger

[57] ABSTRACT

A container for collecting body fluids comprising, a receptacle having a cavity, and a siphon assembly having a pair of opposed spaced walls defining a chamber, a port communicating with the chamber to receive the fluids, and a siphon passageway. The passageway has an upper portion spaced a substantial distance above a lower portion of the chamber and located below an upper portion of the chamber, a first portion connecting the passageway upper portion to the lower portion of the chamber, and a second portion extending downwardly from the passageway upper portion and communicating with the receptacle cavity.

18 Claims, 15 Drawing Figures

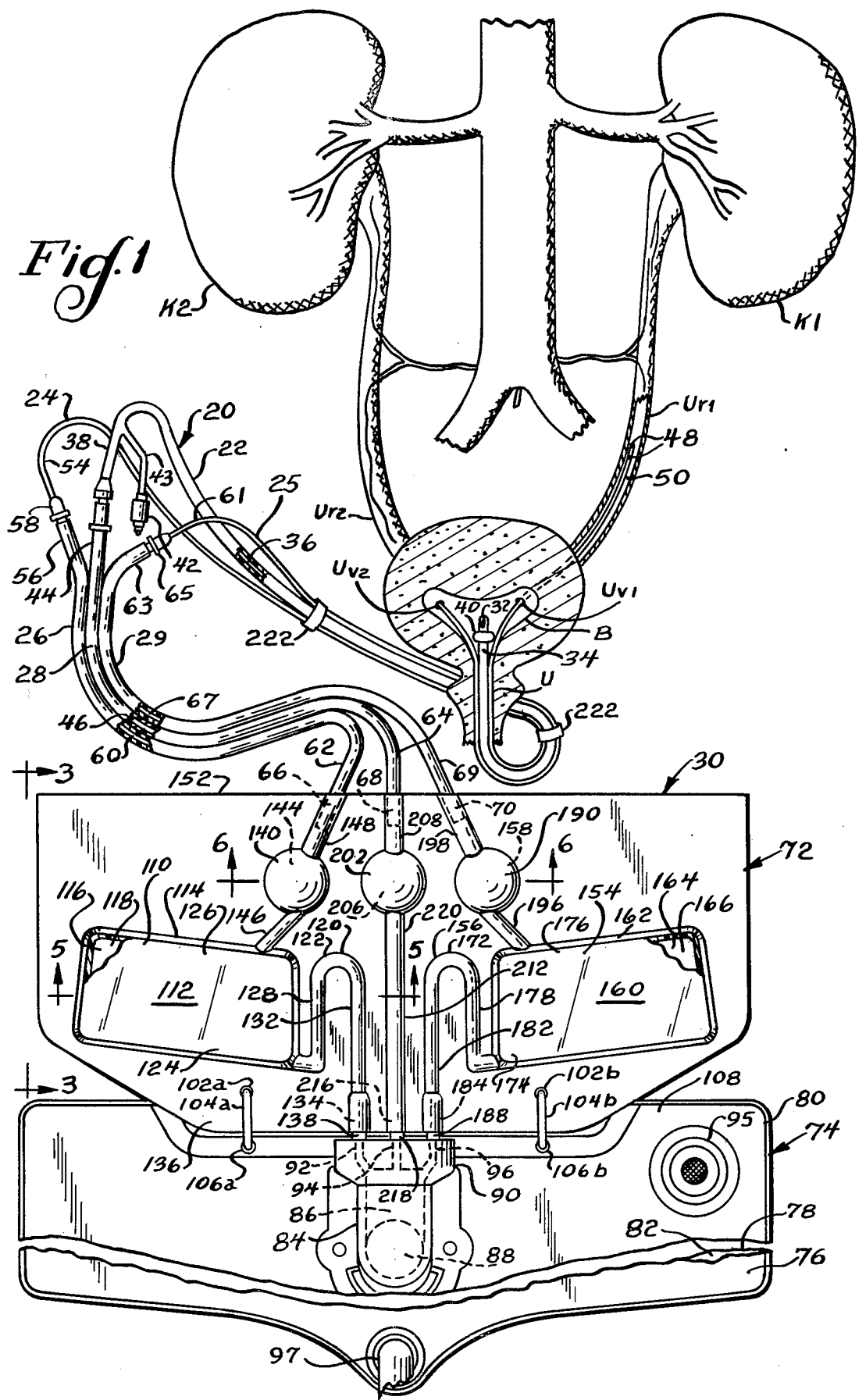

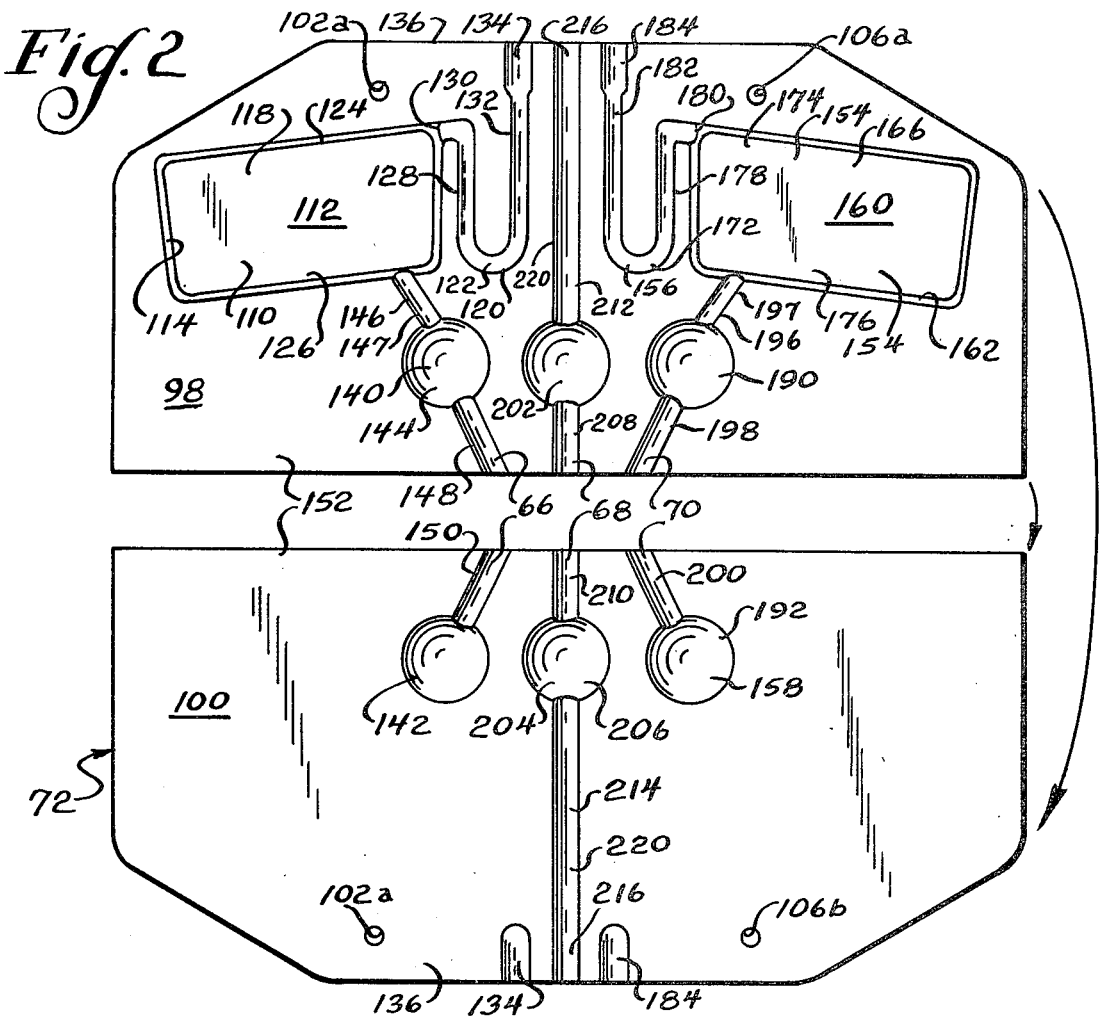
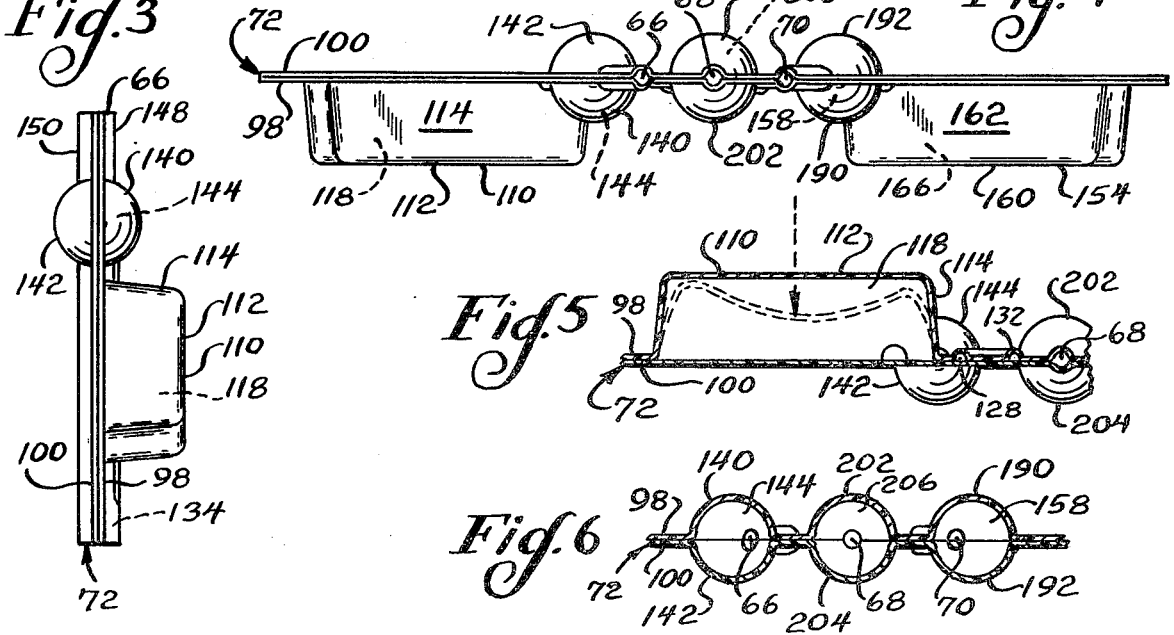

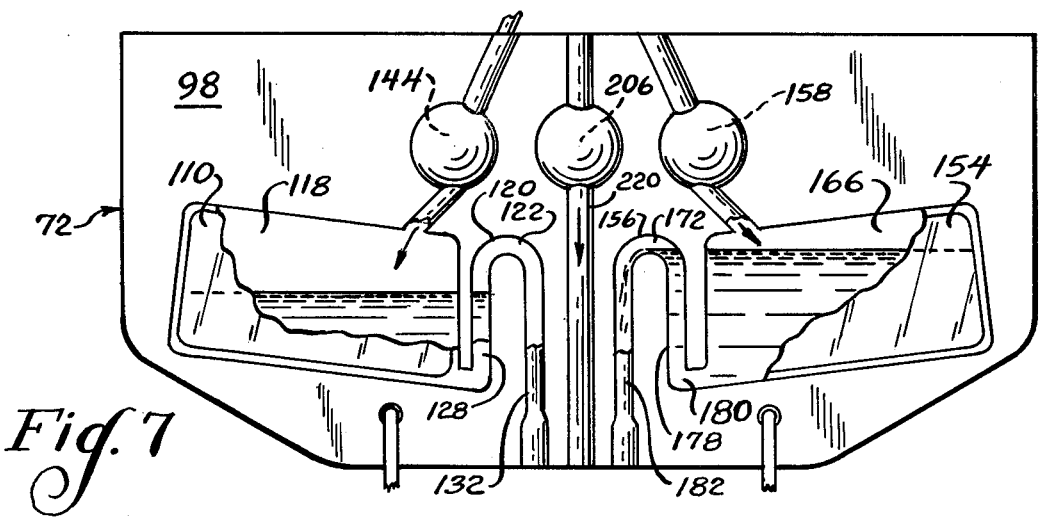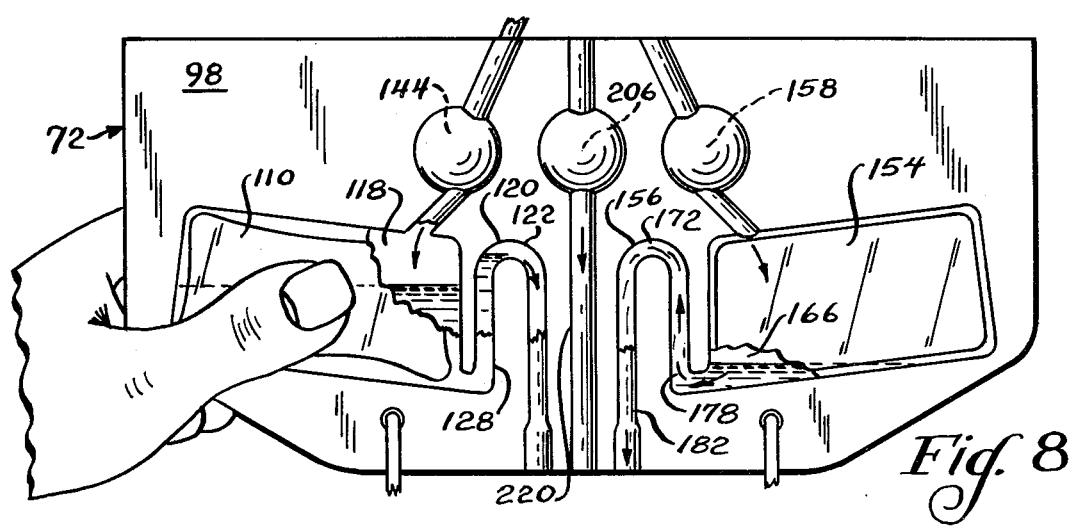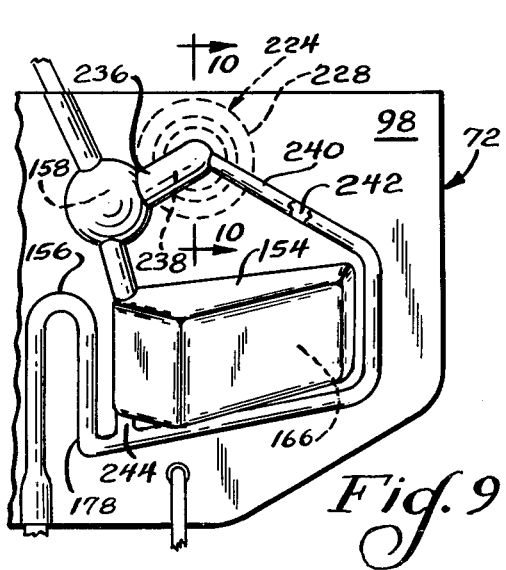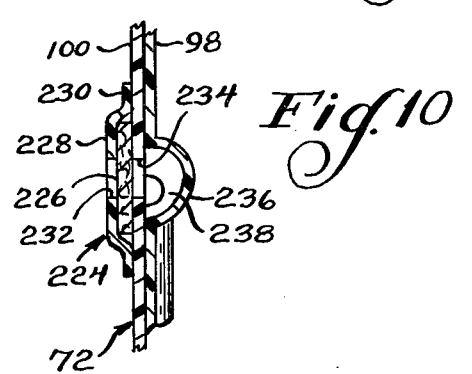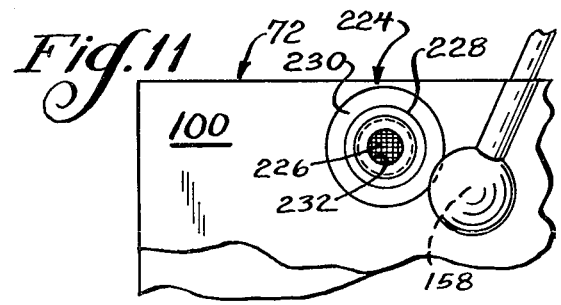

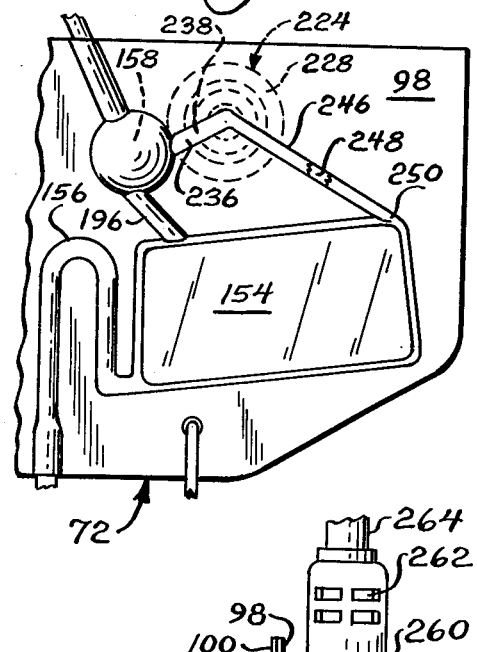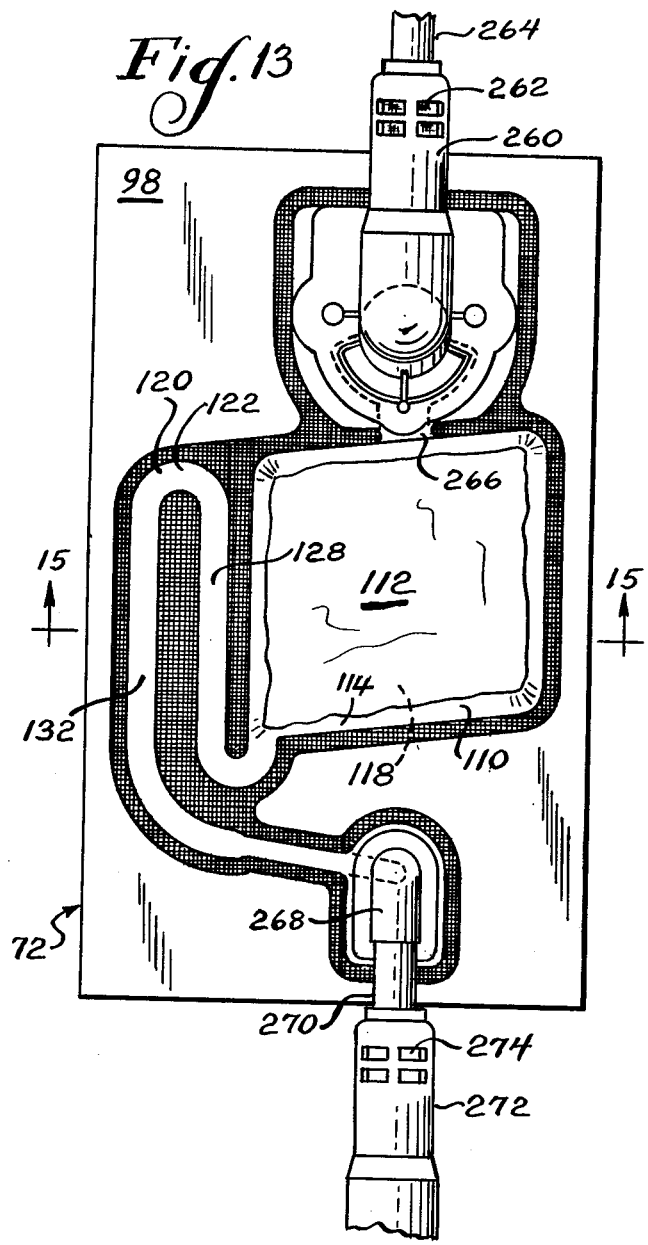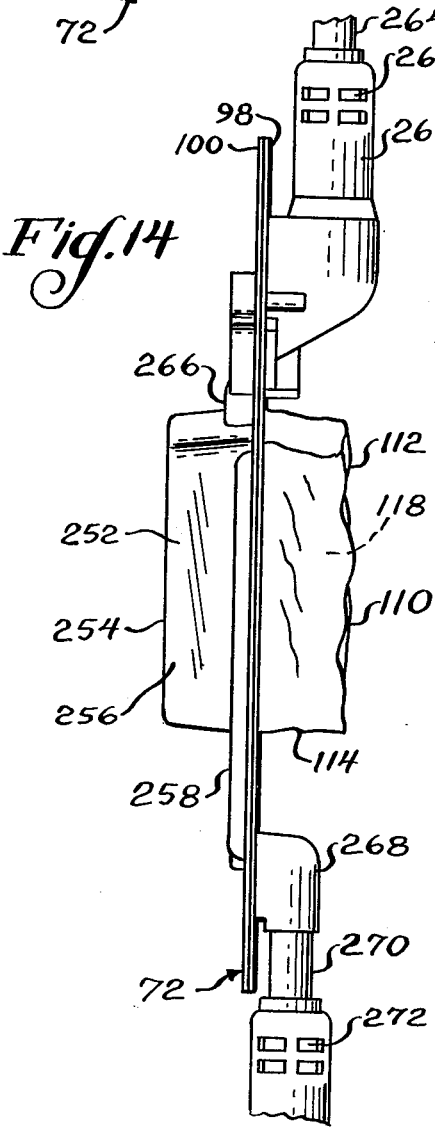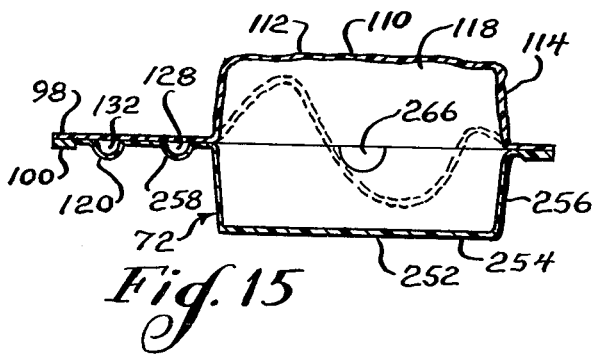

COLLECTION CONTAINER WITH SIPHON ASSEMBLY

BACKGROUND OF THE INVENTION

The present invention relates to liquid drainage systems, and more particularly to liquid collection receptacles.

In the past, catheters have been used to drain urine from a patient's bladder. In such a procedure, a distal end of the catheter, such as a Foley catheter, is inserted through the patient's urethra into the bladder, and a retention balloon adjacent the distal end of the catheter is inflated in the bladder to retain the catheter in place. The catheter has a drainage eye adjacent the distal end of the catheter communicating with a drainage lumen extending from the drainage eye to a proximal end of the catheter which remains outside the patient's body during use of the catheter. Accordingly, urine drains from the bladder through the drainage eye and lumen to the proximal end of the catheter after which the urine is collected in a receptacle.

On occasion it is necessary to drain urine directly from one or both of the patient's ureters or kidneys. For example, subsequent to certain ureterotomy procedures a ureteral catheter is passed through the urethra, bladder, and ureterovesicle junction, such that drainage eyes in the ureteral catheter are located upstream from the surgical site, and possibly in the enlarged renal pelvis adjacent the kidney. Urine drains through the drainage eyes and a drainage lumen extending through the ureteral catheter to a proximal end of the catheter outside the patient's body for collection of the urine. Thus, contact of a substantial amount of urine against the surgical site in the ureter is prevented. The Foley catheter is simultaneously used to drain urine passing from the uncatheterized ureter into the bladder and to drain any residual urine from the catheterized ureter which might eventually leak between the catheter and the ureter.

In the event that surgery has been performed on both ureters a second ureteral catheter is placed in the other ureter, and urine drains through both ureteral catheters, while residual urine is drained from the bladder through the Foley catheter, which may also be utilized to stabilize the ureteral catheters. A pair of ureteral catheters may also be used after surgery on the bladder to prevent urine from passing into the bladder. Similarly, ureteral catheters may be used for both ureters during a partial differential study, where the relative output of urine from both kidneys is determined.

SUMMARY OF THE INVENTION

A principal feature of the present invention is the provision of an improved collection container of simplified construction.

The collection container of the invention comprises a receptacle having a cavity, and a siphon assembly having a first pair of opposed spaced walls defining a chamber, a port communicating with the chamber to receive the fluids, and a siphon passageway having an upper portion spaced a substantial distance above a lower portion of the chamber and located below an upper portion of the chamber, a first portion connecting the passageway upper portion to the lower portion of the chamber, and a second portion extending downwardly from the passageway upper portion and communicating with the receptacle cavity. The siphon assembly has a second pair of opposed spaced walls defining a second chamber, a second port communicating with the second chamber to receive fluids, and a second siphon passageway having an upper portion spaced a substantial distance above a lower portion of the second chamber and located below an upper portion of the second chamber, a first portion connecting the second passageway upper portion to the lower portion of the second chamber, and a second portion extending downwardly from the upper passageway portion of the second passageway and communicating with the receptacle cavity. The siphon assembly has a third passageway extending between upper and lower portions of the assembly and communicating with the receptacle cavity. The container may be utilized in a drainage assembly comprising a plurality of separate catheters which are connected through separate drainage tubes to the first chamber, second chamber, and the third passageway.

A feature of the present invention is that urine drains through separate catheters and drainage tubes to the separate chambers for collection therein, while urine drains through the additional catheter and drainage tube to the third passageway for collection in the receptacle cavity.

Thus, a feature of the present invention is that the urine draining from different sources collects in separate chambers and the cavity.

Still another feature of the invention is that the relative amount of urine drained through each of the catheters may be readily determined by the amount of urine collected in the chambers and cavity, with particular accuracy of the collected urine volumes being determined in the first and second chambers due to a relatively small size of the chambers.

Yet another feature of the invention is that at least one of the opposed walls of the first and second chambers is deformable such that it may be pressed to substantially reduce the volume of the chamber.

Thus, another feature of the invention is that the deformable wall may be pressed to cause passage of urine from the respective chamber through the associated siphon passageway, after which the remaining portion of urine in the chamber is siphoned from the chamber.

Accordingly, a feature of the present invention is that a selected chamber may be readily emptied by pressing the deformable wall in order to reinitiate collection of urine in the selected chamber.

Yet another feature of the invention is that the container automatically siphons urine from the chambers through the siphon passageways when a preselected height of urine collects in the chambers in order to empty the chambers and reinitiate collection of urine in the chambers.

A further feature of the invention is that a single chamber may be utilized in conjunction with the receptacle for purposes of precisely measuring the volume of urine from a single urine source before passing into the receptacle for collection.

Further features will become more fully apparent in the following description of the embodiments of this invention and from the appended claims.

DESCRIPTION OF THE DRAWINGS

In the drawings:

FIG. 1 is a fragmentary plan view, taken partly in section, of an embodiment of a collection container and liquid drainage system of the present invention;

FIG. 2 is a plan view of a pair of plates, taken from the inside, of a header assembly for the container of FIG. 1;

FIG. 3 is an end view of the header assembly taken substantially as indicated along the line 3—3 of FIG. 1;

FIG. 4 is an upper end view of the header assembly of the container of FIG. 1;

FIG. 5 is a fragmentary sectional view taken substantially as indicated along the line 5—5 of FIG. 1;

FIG. 6 is a fragmentary sectional view taken substantially as indicated along the line 6—6 of FIG. 1;

FIGS. 7 and 8 are elevational views, partly broken away, illustrating the container header assembly during urine drainage;

FIG. 9 is a fragmentary elevational view of another embodiment of a header assembly in the container of the present invention;

FIG. 10 is a fragmentary sectional view taken substantially as indicated along the line 10—10 of FIG. 9;

FIG. 11 is a fragmentary back plan view of the header assembly illustrated in FIG. 9;

FIG. 12 is a fragmentary elevational view of a header assembly in another embodiment of the container of the present invention;

FIG. 13 is a fragmentary elevational view of a header assembly in another embodiment of a container of the present invention;

FIG. 14 is a fragmentary side view of the header assembly of FIG. 13; and

FIG. 15 is a sectional view taken substantially as indicated along the line 15—15 of FIG. 13.

DESCRIPTION OF THE PREFERRED EMBODIMENTS

Referring now to FIG. 1, there is shown a liquid drainage system generally designated 20 having a Foley or urinary catheter 22, a ureteral catheter 24, a ureteral catheter 25, three drainage tubes 26, 28, and 29, and a container generally designated 30 of the present invention. The Foley catheter 22 has a drainage eye 32 adjacent a distal end 34 of the catheter, and a drainage lumen 36 extending from the drainage eye 32 to a proximal end 38 of the catheter. The catheter 22 has an inflatable retention balloon 40 adjacent the distal end 34 of the catheter which is inflated through valve means 42 on a sidearm 43 of the catheter and through an inflation lumen (not shown). The proximal end 38 of the catheter 22 is connected to an upstream end 44 of the drainage tube 28 with the drainage lumen 36 of the catheter 22 in communication with a drainage lumen 46 in the drainage tube 28. The ureteral catheter 24 has one or more drainage eyes 48 adjacent a distal end 50 of the catheter, and a drainage lumen extending from the drainage eyes 48 to a proximal end 54 of the catheter. The proximal end 54 of the catheter 24 is connected to an upstream end 56 of the drainage tube 26 by a connector 58 with the drainage lumen in the catheter 24 in communication with a drainage lumen 60 in the drainage tube 26. The catheter 25 is similar to the catheter 24, and has a plurality of drainage eyes adjacent a distal end of the catheter 25 and a drainage lumen extending from the drainage eyes to a proximal end 61 of the catheter 25. The proximal end 61 of the catheter 25 is connected to an upstream end 63 of the drainage tube 29 by a connector 65 with the drainage lumen in the catheter 25 in communication with a drainage lumen 67 in the drainage tube 29. As shown, downstream ends 62, 64, and 69 of the drainage tubes 26, 28 and 29, respectively, are received in and connected to a plurality of ports 66, 68, and 70, respectively, of a header assembly generally designated 72 which supports a receptacle generally designated 74 in the container 30.

The receptacle 74 has a pair of opposed flexible sidewalls 76 and 78 joined together along seal lines 80 extending around the periphery of the receptacle 74, with the walls 76 and 78 defining a chamber 82 for collection of urine in the receptacle 74. The receptacle 74 has a drip chamber 84 secured to an outer surface of the wall 76, with the drip chamber 84 having a cavity 86 communicating with the receptacle chamber 82 through an opening 88 in the wall 76. The receptacle 74 also has a connector 90 secured to the drip chamber 84 and having a plurality of ports 92, 94, and 96 communicating with the cavity 86 of the drip chamber 84. The receptacle 74 may also have a suitable vent 95 for the chamber 82, and a tube 97 for draining liquid from the chamber 82.

With reference to FIGS. 1-6, the header assembly 72 has a first front plate 98, and a second back plate 100, with facing surfaces of the front and back plates 98 and 100 being joined together in generally planar areas through use of suitable means, such as adhesive or heat-sealing. In a preferred form, the front plate 98 is constructed from a relatively elastic plastic material, while the back plate 100 is constructed from a relatively rigid plastic material. With reference to FIG. 1, the joined plates 98 and 100 have a pair of spaced lower openings 102a and 102b, such that the receptacle 74 may be supported by a pair of suitable ties 104a and 104b which pass through the openings 102a and b and through associated openings 106a and 106b in an upper portion 108 of the receptacle 74, such that the receptacle 74 depends from the header assembly 72 during use of the container 30.

With reference to FIGS. 1-6, the front plate 98 has a raised portion or compartment 110 defining an outer wall 112, and a sidewall 114 extending peripherally around the outer wall 112 and connecting the outer wall 112 to the remaining portion of the front plate 98 at the juncture of the front and back plates 98 and 100. Thus, the outer wall 112 and sidewall 114 of the raised compartment 110, together with an opposed wall portion 116 of the back plate 100, define a collection chamber 118 of relatively small volume intermediate the outer wall 112 and opposed wall portion 116. As shown, a raised portion of the front plate 98 also defines a first siphon passageway 120 having an arcuate U-shaped upper portion 122 located substantially above a lower portion 124 of the compartment 110, and located slightly below an upper portion 126 of the compartment 110. The first passageway 120 also has a first portion 128 extending between a port 130 at the lower end 124 of the compartment 110 and the upper passageway portion 122. The first passageway 120 also has a second portion 132 extending downwardly from the upper passageway portion 122 to a port 134 at a lower end 136 of the header assembly 72, with a tubular section 138 connecting the second portion 132 of the first passageway 120 and the port 92 in the connector 90, such that fluid communication is established between the first passageway 120 and the cavity 86 in the drip chamber 84.

The front and back plates 98 and 100 have a pair of opposed hemispherical raised portions 140 and 142, respectively, defining a drip chamber 144 intermediate the plates 98 and 100. The front plate 98 also has a raised portion 146 defining a channel 147 communicating between the drip chamber 144 and the first chamber 118 adjacent the upper end of the compartment 110. As shown, the front and back plates 98 and 100 also have opposed raised portions 148 and 150, respectively, extending from the drip chamber 144 to an upper end 152 of the header assembly 72 and defining the port 66 to receive the downstream end 62 of the drainage tube 26.

The first plate 98 also has a second raised portion or compartment 154, associated second siphon passageway 156, and second drip chamber 158 similar to that previously described in connection with the first compartment 110 and chamber 118. Thus, the second compartment 154 has an outer wall 160, and a sidewall 162 extending around the outer wall 160 and connecting the outer wall 160 to the juncture of the first and second plates 98 and 100, with the outer wall 160 and an opposed wall portion 164 of the second plate 100 defining a second chamber 166 intermediate the first and second plates 98 and 100. The first plate 98 has a raised portion defining an upper portion 172 of the second siphon passageway 156 with the upper portion 172 being located a substantial distance above a lower portion 174 of the second compartment 154, and slightly below an upper portion 176 of the second compartment 154. The second passageway 156 also has a first portion 178 extending between the upper portion 172 and a port 180 adjacent the lower portion 174 of the second compartment 154. The second passageway 156 also has a second portion 182 extending downwardly from the upper portion 172 and defining a port 184 at the lower end 136 of the header assembly 72. The container has a tubular section 188 communicating between the port 184 in the header assembly 72 and the port 96 in the connector 90 in order to establish communication between the second passageway 156 and the cavity 86 in the drip chamber 84.

The first and second plates 98 and 100 have opposed hemispherical portions 190 and 192, respectively, defining a drip chamber 158 above the second compartment 154. As shown, the front plate 98 has a raised portion 196 defining a channel 197 extending between a lower end of the drip chamber 158 and the upper portion 176 of the second compartment 154. Also, the front and back plates 98 and 100 have raised portions 198 and 200, respectively, defining the port 70 at the upper end 152 of the header assembly 72 in order to receive the downstream end 69 of the drainage tube 29.

The first and second plates 98 and 100 have opposed hemispherical raised portions 202 and 204, respectively, defining a third drip chamber 206. The front and back plates 98 and 100 also have raised portions 208 and 210, respectively, defining the port 68 at the upper end 152 of the header assembly 72 in order to receive the downstream end 64 of the drainage tube 28. The first and second plates 98 and 100 also have opposed raised portions 212 and 214 extending from a lower end of the third drip chamber 206 to the lower end 136 of the header assembly 72, and defining a third passageway 220 and lower port 216 to receive a tubular section 218 which communicates between the third passageway 220 and the port 94 in the connector 90, such that communication is established between the third passageway 220 and the cavity 86 in the drip chamber 84.

In operation of the drainage system, the physician uses a cystoscope to locate the ureteroversicle junction Uv1 leading from the bladder B to the ureter Ur1, after which he threads the ureteral catheter 24 through the urethra U, and the bladder B into the ureter UR1 with the drainage eyes 48 located in the ureter Ur1. The physician then removes the crystoscope over the ureteral catheter 24, and uses a similar procedure to place the ureteral catheter 25 through the urethra U and the ureteroversicle junction Uv2 into the ureter Ur2. Next, the physician passes the distal end 34 of the Foley catheter 22 through the urethra U into the bladder B, after which the retention balloon 40 is inflated in the bladder B through the valve means 42 of the catheter sidearm 43 by suitable means, such as a syringe (not shown). The inflated balloon 40 retains the catheter 22 in place, and also engages against the ureteral catheters 24 and 25 to assist in retaining the ureteral catheters at the proper location in the ureters. The ureteral catheters 24 and 25 may be secured to the Foley catheter 22 outside the patient's body by suitable means, such as tape strips 222, in order to retain the ureteral catheters to the Foley catheter. Thus, if tension is applied to the proximal ends of the ureteral catheters, the tension is transmitted by the tape strips 222 to the Foley catheter 22, and the retention balloon 40 prevents dislodgment of the ureteral catheters from the ureters. The proximal end 54 of the ureteral catheter 24 is then connected to the upstream end 56 of the drainage tube 26 by the connector 58, the proximal end 61 of the ureteral catheter 25 is connected to the upstream end 63 of the drainage tube 29 by the connector 65, while the proximal end 38 of the Foley catheter 22 is connected to the upstream end 44 of the drainage tube 28.

Thus, urine passing from the kidney K1 through the ureter Ur1 passes through the drainage eyes 48 of the ureteral catheter 24, through the drainage lumen of the ureteral catheter, the drainage lumen 60 of the drainage tube 26, and through the drip chamber 144 into the first chamber 118 for collection therein. Similarly, urine from the kidney K2 passes through the ureter Ur2 into the drainage eyes of the ureteral catheter 25, through the drainage lumen of the ureteral catheter 25, the drainage lumen 67 of the drainage tube 29, and the drip chamber 158 into the second chamber 166 for collection therein. Residual urine which may leak around the ureteral catheters 24 and 25 into the bladder B drain through the drainage eye 32 and drainage lumen 36 of the urinary catheter 22, through the drainage lumen 46 of the drainage tube 26, the drip chamber 206 and third passageway 220 of the header assembly 72, and through the drip chamber 84 of the receptacle 74 into the receptacle chamber 82 for collection therein.

Accordingly, urine from the ureters Ur1 and Ur2 and the bladder B are separately collected in an aseptic manner in the chambers 118 and 166 of the header assembly 72, and in the chamber 82 of the receptacle 74. The relative quantity of the separately drained urine may be readily checked by viewing the level of collected urine through transparent sidewalls of the header assembly 72 and the receptacle 74, with suitable indicia being placed on the compartments 110 and 154, and the front wall 76 of the receptacle 74 in order to readily determine the volume. The volume of the first and second chambers 118 and 166 is relatively small compared to the total volume of the receptacle chamber 82, such that relatively accurate urine volumes may be ascertained in the first and second chambers 118 and 166.

The features of the container will be more fully explained in connection with FIGS. 7 and 8. Thus, with reference to the right-hand portion of FIG. 7, as urine collects in the second chamber 166, the urine also passes through the lower port 180 into the first portion 178 of the second passageway 156. When the height of liquid in the second compartment 166 attains the level of the passageway upper portion 172, the urine begins to flow through the upper portion 172 into the second passageway portion 182. Thus, with reference to the right-hand portion of FIG. 8, the urine is siphoned from the second chamber 166 through the second passageway 156 into the chamber of the lower receptacle until the second chamber 166 is substantially empty, with the lower walls of the chambers being tilted toward the lower ports to facilitate the emptying procedure. Accordingly, the second chamber fills to a predetermined height and volume during urine drainage, and the second chamber automatically empties through the second passageway 156 when the predetermined height has been attained, with this procedure automatically repeating itself each time the second chamber has been filled with the predetermined volume of urine. Of course, the first chamber operates in the same manner to automatically empty the chamber through the first passageway 120 when a predetermined height and volume of liquid has been collected in the first chamber 118.

The liquid level of the first chamber 118 in the left-hand portion of FIG. 7 is illustrated below the predetermined height necessary to cause automatic emptying of the first chamber 118. However, with reference to the left-hand portion of FIG. 8, the chamber may be emptied at a desired time by squeezing the walls of the first compartment 110 in order to reduce the volume in the first chamber 118 until the urine passes from the first chamber 118 through the upper portion 122 of the first passageway 120 to initiate the siphoning of urine from the first chamber 118. Accordingly, once the first compartment 110 has been squeezed a sufficient amount to cause passage of liquid through the upper portion 122 of the first passage 120, the liquid continues to flow through the first passageway 120 into the receptacle chamber for collection therein while the chamber 118 of the first compartment 110 is emptied of liquid. Of course, the chamber 166 of the second compartment 154 may be emptied at a desired time by squeezing the compartment 154 in order to initiate siphoning of liquid from the second chamber 166 through the second passageway 156 into the lower receptacle chamber.

Thus, in accordance with the present invention, urine is separately collected in the first and second chambers 118 and 166 in order to precisely ascertain the volume of liquid during a selected time. If the liquid reaches a predetermined height in the chambers, the liquid automatically passes from the chambers into the lower receptacle chamber until the associated header chamber is emptied, after which collection of liquid in the empty chamber begins anew. Further, the header chambers may be emptied at a desired time by pressing the elastic wall of the associated compartment, such that a new collection period may be initiated at the desire of the user.

Another embodiment of the present invention is illustrated in FIGS. 9–11, in which like reference numerals designate like parts. In this embodiment, the header assembly 72 has a vent 224 secured to the back plate 100. The vent 224 comprises a circular air permeable filter 226 which permits passage of air through the filter 226 while filtering bacteria from the air. The header assembly 72 has a retaining ring 228 overlying the filter 226, and having its edges 230 secured to the back plate 100 peripherally around the filter 226. Also, as shown, the ring 228 has a central opening 232 extending through the ring 228 and communicating with the filter 226 to permit passage of air through the ring 228 to the filter 226. Further, the back plate 100 has an opening 234 extending through the back plate 100 and communicating with the filter 226 in order to permit passage of air through the filter 226 and the back plate 100.

The front plate 98 has a raised portion 236 defining a channel 238 communicating between the drip chamber 158 and the vent 224. Also, the front plate 98 has a raised portion 240 defining a channel 242 which communicates with the channel 238 at its upper end. The channel 242 extends around the side and lower portion of the second compartment 154 where the channel 242 joins the second passageway 156 at the lower end of the first passageway portion 178, with the second passageway 156 and the channel 242 being connected to the lower end of the second chamber in the compartment 154 through a raised portion 244 in the front plate 98. Accordingly, communication is established between the vent 224, the drip chamber 158, the second chamber 166, and the second passageway 156 to facilitate passage of liquid into and out of the second chamber 166 during drainage and collection of urine. Of course, the first compartment and associated chamber may have a vent of similar type. In an alternative form, as shown in FIG. 12, the front plate 98 may have a raised portion 246 defining a channel 248 which extends from the filter 224 to a remote upper end 250 of the second compartment 154, such that the drip chamber 158 and the filter 224 are connected at spaced locations to the upper end of the chamber in the second compartment 154.

Another embodiment of the present invention is illustrated in FIGS. 13–15, in which like reference numerals designate like parts. In this embodiment, the header assembly 72 has front and back plates 98 and 100, respectively, defining a single compartment 110. As before, the front plate 98 may be made from a relatively elastic plastic material, while the back plate 100 may be made from a relatively rigid plastic material. The raised portion or compartment of the front plate 98 has an outer wall 112 and a peripheral sidewall 114 connecting the outer wall 112 to the juncture of the first and second plates 98 and 100, as previously described. Also, if desired, the back plate 100 may have a raised portion 252 defining an outer wall 254 and a sidewall 256 extending peripherally around the outer wall 254 and connecting the outer wall 254 to the juncture of the first and second plates 98 and 100. Thus, the raised portion 110 of the front plate 98 and the raised portion 252 of the back plate 100 define a chamber 118. As before, the volume of the chamber 118 may be substantially reduced by depressing the raised portion 110 toward the back plate 100.

The back plate 100 may have a raised portion 258 defining the siphon passageway 120 with an upper portion 122, a first portion 128 extending between the upper passageway portion 122 and a lower portion of the chamber 118, and a second passageway portion 132 extending downwardly from the upper passageway portion 122.

As shown, the header assembly 72 may have a drip chamber 260 secured to the front wall 98 and having a vent 262 of air permeable, bacteria impermeable filter material, communicating with the inside of the drip chamber 260. The upper end of the drip chamber 260 is connected to the downstream end of a conduit 264, and the drip chamber 260 is in fluid communication through a channel 266 with an upper end of the compartment chamber 118. The header assembly 72 may have a connecter 268 in communication with the lower end of the second passageway portion 132, and with the connecter 268 being connected through a conduit 270 to a drip chamber 272, with the drip chamber 272 having a suitable vent 274. In turn, the drip chamber 272 may be connected to the chamber of a lower receptacle for collection of liquid therein. The upper conduit 264 may be connected to a suitable catheter, such as a Foley catheter during catheterization, such that urine flows from the catheter through the drainage tube 264 and the drip chamber 260 into the chamber 118 of the compartment 110.

Thus, the compartment 110 of the header assembly 72 may be utilized in the form of a urine meter to more precisely determine the volume of urine which flows into the compartment chamber 118. The urine may be collected in the compartment for a period of time, after which the front wall of the compartment 110 may be depressed in order to cause the collected urine to siphon out of the chamber 118 through the passageway 120, through the connector 268, and the drip chamber 272 into the relatively large chamber of the lower container for collection therein, after which collection of urine begins anew in the compartment chamber 118. Also, as previously described, if the height of liquid in the compartment chamber 118 attains the level of the passageway upper portion 122, the urine siphons from the chamber 118 through the passageway 120 in order to automatically empty the chamber, and the urine begins to collect again in the compartment chamber 118.

The foregoing detailed description is given for clearness of understanding only, and no unnecessary limitations should be understood therefrom, as modifications will be obvious to those skilled in the art.

I claim:

1. A container for collecting body fluids comprising: a receptacle having a cavity; and a siphon assembly having a pair of opposed spaced walls and a sidewall defining an assembly chamber, a port communicating with the assembly chamber to receive the fluids, and wall means defining a siphon passageway having an upper portion spaced a substantial distance above a lower portion of the assembly chamber and located below an upper portion of the assembly chamber, a first portion connecting the passageway upper portion to the lower portion of the assembly chamber, and a second portion extending downwardly from the passageway upper portion and communicating with the receptacle cavity, with at least one of said opposed walls being constructed from a flexible material, such that the one wall may be pressed toward the other of said walls to substantially reduce the volume in the assembly chamber, including a drip chamber located above the assembly chamber, and a first channel communicating between the drip chamber and the port adjacent the upper portion of the assembly chamber.

2. The container of claim 1 wherein said assembly chamber has a volume substantially less than the volume of said cavity.

3. The container of claim 1 including vent means communicating with said port.

4. The container of claim 1 including a drip chamber communicating with said port.

5. The container of claim 1 including a drip chamber connecting said second portion to the receptacle cavity.

6. The container of claim 1 including vent means communicating with the drip chamber.

7. The container of claim 1 wherein the siphon assembly includes a second pair of opposed spaced walls defining a second chamber, a port communicating with the second chamber to receive fluids, and a second siphon passageway having an upper portion spaced a substantial distance above a lower portion of the second chamber and located below an upper portion of the second chamber, a first portion connecting the passageway upper portion to the lower portion of the second chamber, and a second portion extending downwardly from the upper passageway portion and communicating with the receptacle cavity.

8. A container for collecting body fluids, comprising:
a receptacle having a cavity; and
a header assembly for said receptacle having a pair of first and second plates joined together in areas, with the first plate being constructed from an elastic material and having a raised portion comprising an outer wall and sidewalls extending around the outer wall and connecting the outer wall to the juncture of the first and second plates, with said outer wall being spaced from an opposed wall of the second plate, such that said outer and sidewalls of the first plate and the opposed wall of the second plate define a chamber intermediate the first and second plates, with the outer and sidewalls of the first plate being deformable by pressing to substantially reduce the volume of the chamber, at least one of said plates including a raised portion defining a siphon passageway having an upper U-shaped portion spaced a substantial distance above a lower portion of the chamber and located below an upper portion of the chamber, a first portion connecting the upper passageway portion to the lower portion of the chamber, and a second portion extending downwardly from the upper passageway portion, and means for connecting the second passageway portion to the receptacle cavity, said second plate including a raised portion comprising said opposed wall and sidewalls extending around said opposed wall, with said sidewalls spacing said opposed wall from the juncture of the first and second plates.

9. A container for collecting body fluids, comprising:
a receptacle having a cavity;
a header assembly for said receptacle having a pair of first and second plates joined together in areas, with the first plate being constructed from an elastic material and having first and second raised portions spaced from the second plate to define separate first and second chambers, with the raised portions being deformable by pressing to substantially reduce the volume of the chambers, said plates defining first and second siphon passageways associated respectively with the first and second chambers, with the passageways each having upper portions spaced slightly below upper portions of the respective chambers, first portions connecting the upper passageway portions to lower portions of the respective chambers, and second portions extending downwardly from the respective upper passageway portions; and means for connecting the second portions of the first and second passageways to the receptacle cavity.

10. A container for collecting body fluids, comprising:

a receptacle having a cavity; and a siphon assembly having a pair of opposed spaced walls and a sidewall defining an assembly chamber, a port communicating with the assembly chamber to receive the fluids, and wall means defining a siphon passageway having an upper portion spaced a substantial distance above a lower portion of the assembly chamber and located below an upper portion of the assembly chamber, a first portion connecting the passageway upper portion to the lower portion of the assembly chamber, and a second portion extending downwardly from the passageway upper portion and communicating with the receptacle cavity, with at least one of said opposed walls being constructed from a flexible material, such that the one wall may be pressed toward the other of said walls to substantially reduce the volume in the assembly chamber;

a drip chamber located above the assembly chamber;

a first channel communicating between the drip chamber and the port adjacent the upper portion of the assembly chamber;

vent means communicating with the drip chamber; and a second channel communicating between the vent means and a second port adjacent the upper portion of the assembly chamber.

11. A container for collecting body fluids, comprising:

a receptacle having a cavity; and a siphon assembly having a pair of opposed spaced walls and a sidewall defining an assembly chamber, a port communicating with the assembly chamber to receive the fluids, and wall means defining a siphon passageway having an upper portion spaced a substantial distance above a lower portion of the assembly chamber and located below an upper portion of the assembly chamber, a first portion connecting the passageway upper portion to the lower portion of the assembly chamber, and a second portion extending downwardly from the passageway upper portion and communicating with the receptacle cavity, with at least one of said opposed walls being constructed from a flexible material, such that the one wall may be pressed toward the other of said walls to substantially reduce the volume in the assembly chamber;

a drip chamber located above the assembly chamber;

a first channel communicating between the drip chamber and the port adjacent the upper portion of the assembly chamber;

vent means communicating with the drip chamber; and a second channel communicating between the vent means and the lower portion of said assembly chamber.

12. The container of claim 11 wherein said assembly chamber has a lower port communicating with the first passageway portion and a lower portion of said second channel.

13. A container for collecting body fluids, comprising:

a receptacle having a cavity; and a header assembly for said receptacle having a pair of first and second plates joined together in areas, with the first plate being constructed from an elastic material and having a raised portion comprising an outer wall and sidewalls extending around the outer wall and connecting the outer wall to the juncture of the first and second plates, with said outer wall being spaced from an opposed wall of the second plate, such that said outer and sidewalls of the first plate and the opposed wall of the second plate define a chamber intermediate the first and second plates, with the outer and sidewalls of the first plate being deformable by pressing to substantially reduce the volume of the chamber, at least one of said plates including a raised portion defining a siphon passageway having an upper U-shaped portion spaced a substantial distance above a lower portion of the chamber and located below an upper portion of the chamber, a first portion connecting the upper passageway portion to the lower portion of the chamber, and a second portion extending downwardly from the upper passageway portion, and means for connecting the second passageway portion to the receptacle cavity, with at least one of said plates including a raised portion defining a drip chamber and a channel connecting said drip chamber to the upper portion of the chamber.

14. The container of claim 13 wherein said first and second plates include opposed raised portions defining said drip chamber.

15. A container for collecting body fluids, comprising:

a receptacle having a cavity;

a header assembly for said receptacle having a pair of first and second plates joined together in areas, with the first plate being constructed from an elastic material and having first and second raised portions spaced from the second plate to define separate first and second chambers, with the raised portions being deformable by pressing to substantially reduce the volume of the chambers, said plates defining first and second siphon passageways associated respectively with the first and second chambers, with the passageways each having upper portions spaced slightly below upper portions of the respective chambers, first portions connecting the upper passageway portions to lower portions of the respective chambers, and second portions extending downwardly from the respective upper passageway portion, said plates defining first and second drip chambers, and first and second channels connecting the drip chambers to the respective first and second chambers; and means for connecting the second portions of the first and second passageways to the receptacle cavity.

16. The container of claim 15 wherein the plates define a third drip chamber, and a third passageway extending downwardly from the third drip chamber, and including means connecting the third passageway to the receptacle cavity.

17. A container for collecting body fluids, comprising:

a receptacle having a cavity; and a siphon assembly having a pair of opposed spaced walls and a sidewall defining an assembly chamber, a port communicating with the assembly chamber to receive the fluids, and wall means defining a siphon passageway having an upper portion spaced a substantial distance above a lower portion of the assembly chamber and located below an upper portion of the assembly chamber, a first portion connecting the passageway upper portion to the lower portion of the assembly chamber, and a second portion extending downwardly from the passageway upper portion and communicating with the receptacle cavity, with at least one of said opposed walls being constructed from a flexible material, such that the one wall may be pressed toward the other of said walls to substantially reduce the volume in the assembly chamber, said siphon assembly including a second pair of opposed spaced walls and a sidewall defining a second chamber, a port communicating with the second chamber to receive fluids, and wall means defining a second siphon passageway having an upper portion spaced a substantial distance above a lower portion of the second chamber and located below an upper portion of the second chamber, a first portion connecting the passageway upper portion to the lower portion of the second chamber, and a second portion extending downwardly from the upper passageway portion and communicating with the receptacle cavity, and further including a third passageway extending between an upper and lower portion of the assembly and communicating with the receptacle cavity.

18. The container of claim 17 including first, second, and third catheters, and including first, second and third conduits, said first conduit communicating between said first catheter and the port of the assembly chamber, said second conduit communicating between the second catheter and the port of the second chamber, and said third conduit communicating between the third catheter and the third passageway.

* * * * *